US012648896B2

(12) United States Patent
Nagare et al.

(10) Patent No.: US 12,648,896 B2
(45) Date of Patent: *Jun. 9, 2026

(54) EMULSION COSMETIC

(71) Applicant: Shiseido Company, Ltd., Tokyo (JP)

(72) Inventors: Yuko Nagare, Tokyo (JP); Kei Ujimoto, Tokyo (JP); Kouichi Nagai, Tokyo (JP); Ryoya Ito, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 94 days.

This patent is subject to a terminal disclaimer.

(21) Appl. No.: 17/267,319

(22) PCT Filed: Aug. 9, 2019

(86) PCT No.: PCT/JP2019/031595

§ 371 (c)(1),
(2) Date: Feb. 9, 2021

(87) PCT Pub. No.: WO2020/032241

PCT Pub. Date: Feb. 13, 2020

(65) Prior Publication Data

US 2021/0338544 A1     Nov. 4, 2021

(30) Foreign Application Priority Data

Aug. 10, 2018     (JP) ................................. 2018-151679

(51) Int. Cl.

| | |
|---|---|
| *A61K 8/06* | (2006.01) |
| *A61K 8/35* | (2006.01) |
| *A61K 8/37* | (2006.01) |
| *A61K 8/39* | (2006.01) |
| *A61K 8/86* | (2006.01) |
| *A61Q 17/04* | (2006.01) |

(52) U.S. Cl.

CPC ................ *A61K 8/064* (2013.01); *A61K 8/35* (2013.01); *A61K 8/37* (2013.01); *A61K 8/39* (2013.01); *A61K 8/86* (2013.01); *A61Q 17/04* (2013.01); *A61K 2800/522* (2013.01); *A61K 2800/591* (2013.01)

(58) Field of Classification Search

CPC .......... A61K 8/064; A61K 8/062; A61K 8/37; A61K 8/03; A61K 8/39; A61K 8/86; A61K 8/90; A61K 2800/262; A61K 2800/522; A61K 2800/591; A61Q 17/04

See application file for complete search history.

(56) References Cited

U.S. PATENT DOCUMENTS

| | | | | |
|---|---|---|---|---|
| 8,182,795 B2 * | 5/2012 | Takakura | ................. | A61K 8/86 |
| | | | | 424/59 |
| 2007/0178053 A1 * | 8/2007 | Franklin | .................. | A61K 8/33 |
| | | | | 424/47 |
| 2010/0209365 A1 * | 8/2010 | Takakura | ............... | A61K 8/375 |
| | | | | 424/59 |
| 2017/0333301 A1 * | 11/2017 | Yamaki | .................... | A61K 8/06 |
| 2018/0271755 A1 * | 9/2018 | Yamaki | .................. | A61Q 17/04 |
| 2018/0289610 A1 | 10/2018 | Yamaki et al. | | |
| 2021/0338545 A1 * | 11/2021 | Ujimoto | ................. | A61K 8/064 |

FOREIGN PATENT DOCUMENTS

| | | |
|---|---|---|
| EP | 1 920 762 A1 | 5/2008 |
| EP | 2 181 697 A2 | 5/2010 |
| EP | 3 213 741 A1 | 9/2017 |
| EP | 3 213 742 A1 | 9/2017 |
| EP | 3 357 484 A1 | 8/2018 |
| WO | WO 2016/068298 A1 * | 5/2016 |
| WO | WO 2016/068299 A1 * | 5/2016 |
| WO | WO-2017/057676 A1 | 4/2017 |

OTHER PUBLICATIONS

Database GNPD [Online] Mintel, "Perfect UV Protector SPF 50+/PA++++ for Sensitive Skin & Children," Shiseido, Jun. 16, 2016, Database accession No. 4057965, XP055904718, 6 pages.
Database GNPD [Online] Mintel, "Protection Lotion SPF 30," Shiseido, Jul. 13, 2015, Database Accession No. 3336055, XP055641565, 6 pages.

* cited by examiner

*Primary Examiner* — Hong Yu
(74) *Attorney, Agent, or Firm* — Foley & Lardner LLP

(57) ABSTRACT

An objective of the present invention is to provide an emulsion cosmetic having the innovative, unprecedented property in which the ultraviolet protection effects do not decrease, and conversely increase, due to heat applied in a usage environment. The present invention pertains to an emulsion cosmetic comprising (A) an ultraviolet protectant, (B) a prescribed alkylene oxide derivative, and (C) an ester oil.

9 Claims, No Drawings

EMULSION COSMETIC

CROSS-REFERENCE TO RELATED APPLICATIONS

This application is the U.S. National Stage of PCT/JP2019/031595, filed Aug. 9, 2019, which claims priority to JP 2018-151679, filed Aug. 10, 2018.

TECHNICAL FIELD

The present invention relates to an emulsion cosmetic having sunscreen effects. More specifically, the present invention relates to a cosmetic having the unprecedented property in which heating increases the ultraviolet protection effects over those immediately after applying the cosmetic.

BACKGROUND ART

Cosmetics having sunscreen effects have the effects of reducing the amount of ultraviolet rays reaching the skin on which the cosmetics have been applied and thereby suppressing the harmful impact thereof on the skin due to the action of ultraviolet absorbing agents or ultraviolet scattering agents blended into the cosmetics.

As an indicator of the ultraviolet protection effects of cosmetics, Sun Protection Factor (SPF) is the most widely known, representing the ultraviolet protection effects as an SPF value (for example, "SPF 30", etc.). In Japan, PFA (Protection Factor of UVA) or UVAPF (UVA Protection Factor of product) is used for ultraviolet rays in the UVA range, and the degree of UVA protection effects of a product is represented by PA (Protection grade of UVA) class ("PA+++", etc.), which is based on the PFA or the UVAPF. In the United States, Critical Wavelength (CW), which indicates the balance of UVA and UVB protection effects, is used.

In recent years, in order to suppress the harmful impact of ultraviolet rays on the skin, cosmetics that provide high ultraviolet protection effects across a wide wavelength range from the UVA to the UVB ranges have come to be sought. For example, sunscreen products boasting SPF factors of 50 or higher (50+) and PA++++ have come onto the market.

The ultraviolet protection effects due to sunscreen products are obtained by the ultraviolet protectants, i.e., by the ultraviolet absorbing agents or ultraviolet scattering agents that are blended therein. However, ultraviolet absorbing agents include some in which the ultraviolet absorption performance decreases due to irradiation by light (photodegradation). Additionally, ultraviolet absorbing agents and ultraviolet scattering agents can flow away from the skin surface upon coming into contact with moisture.

Many improvements have been proposed for suppressing the photodegradation of ultraviolet protection effects (Patent Document 1), and regarding water resistance, a cosmetic having the innovative property in which contact with moisture does not decrease the ultraviolet protection effects but conversely increases the protection effects has been developed (Patent Document 2).

Meanwhile, as with light and moisture, decreases in ultraviolet protection effects due to heat cannot be ignored. In general, when heat is applied to a cosmetic that has been applied to skin, the ultraviolet absorbing agents and other components contained in the cosmetic are degraded, thereby decreasing the ultraviolet protection effects. However, regarding heat, although there are examples in which the impact of heat, for example, on the emulsion stability of emulsion cosmetics including cosmetics have been considered (Patent Document 3), changes in the ultraviolet protection effects due to heat have not been considered until now, and cosmetics having the purpose of suppressing decreases in ultraviolet protection effects due to heat have not previously been proposed.

RELATED ART

Patent Documents

Patent Document 1: WO 2017/057676
Patent Document 2: WO 2016/068300
Patent Document 3: JP 4397286 B

SUMMARY OF THE INVENTION

Problem to be Solved by the Invention

The present invention is based on the discovery, in a research process for developing a cosmetic having ultraviolet protection effects, that ultraviolet protection effects do not decrease, but conversely increase, due to heat applied in the usage environment, and an objective is to provide an emulsion cosmetic having the innovative, unprecedented property in which the ultraviolet protection effects increase due to heat.

Means for Solving the Problem

As a result of performing diligent research towards solving the above-mentioned problem, the present inventors discovered that an emulsion cosmetic having the novel properties that are the above-mentioned objective can be obtained by blending an ultraviolet protectant, a specific alkylene oxide derivative and an ester oil, thereby completing the present invention.

In other words, the present invention provides an emulsion cosmetic comprising
(A) an ultraviolet protectant;
(B) an alkylene oxide derivative represented by the following formula (I):

$$R_1O-[(AO)_m(EO)_n]-R_2 \qquad (I)$$

wherein $R_1$ and $R_2$, each independently, denote a hydrogen atom or a hydrocarbon group having one to four carbon atoms, AO denotes an oxyalkylene group having three or four carbon atoms, EO denotes an oxyethylene group, m is at least 1 and represents the average number of moles of AO added, n is at least 1 and represents the average number of moles of EO added, and $m+n \leq 40$; and
(C) an ester oil.

Effects of the Invention

With the emulsion cosmetic of the present invention, due to the above-mentioned features, rather than the ultraviolet protection effects being degraded when exposed to heat during actual use, the ultraviolet protection effects can be significantly increased over those immediately after the cosmetic has been applied to the skin. In other words, the emulsion cosmetic according to the present invention is an innovative cosmetic having the property, contrary to conventional expectations, in which heat, which had been considered to cause degradation of the effects in conventional cosmetics, conversely increase the ultraviolet protection effects.

MODES FOR CARRYING OUT THE INVENTION

The cosmetic of the present invention is characterized by comprising (A) an ultraviolet protectant, (B) a prescribed alkylene oxide derivative, and (C) an ester oil. Hereinafter, the components constituting the emulsion cosmetic of the present invention will be described in detail.

<(A) Ultraviolet Protectant (Ultraviolet Absorbing Agent and/or Ultraviolet Scattering Agent)>

The (A) ultraviolet protectant (hereinafter sometimes referred to simply as "component (A)") blended into the emulsion cosmetic of the present invention refers to an ultraviolet absorbing agent and/or an ultraviolet scattering agent, and a type that is normally blended into cosmetics may be used.

The ultraviolet absorbing agents that can be used in the present invention are not particularly limited, and include a wide range of ultraviolet absorbing agents that are generally used in cosmetics. For example, they include benzoic acid derivatives, salicylic acid derivatives, cinnamic acid derivatives, dibenzoyl methane derivatives, β,β-diphenyl acrylate derivatives, benzophenone derivatives, benzylidene camphor derivatives, phenylbenzimidazole derivatives, triazine derivatives, phenylbenzotriazole derivatives, anthranil derivatives, imidazoline derivatives, benzalmalonate derivatives, 4,4-diaryl butadiene derivatives and the like. Hereinafter, specific examples and product names will be mentioned, but there is no limitation thereto.

Examples of benzoic acid derivatives include ethyl para-aminobenzoate (PABA), ethyl-dihydroxypropyl PABA, ethylhexyl-dimethyl PABA (e.g. "Escalol 507"; ISP), glyceryl PABA, PEG-25-PABA (e.g. "Uvinul P25"; BASF), diethylamino hydroxybenzoyl hexyl benzoate (e.g. "Uvinul A Plus") and the like.

Examples of salicylic acid derivatives include homosalate ("Eusolex HMS"; Rona/EM Industries), ethylhexyl salicylate or octyl salicylate (e.g. "Neo Heliopan OS"; Haarmann & Reimer), dipropylene glycol salicylate (e.g. "Dipsal"; Scher), TEA salicylate (e.g. "Neo Heliopan TS"; Haarmann & Reimer) and the like.

Examples of cinnamic acid derivatives include octyl methoxycinnamate or ethylhexyl methoxycinnamate (e.g. "Parsol MCX"; DSM Nutrition Japan), isopropyl methoxycinnamate, isoamyl methoxycinnamate (e.g. "Neo Heliopan E1000"; Haarmaan & Reimer), cinnoxate, DEA methoxycinnamate, diisopropyl methyl cinnamate, glyceryl ethylhexanoate dimethoxycinnamate, di-(2-ethylhexyl)-4'-methoxybenzalmalonate and the like.

Examples of dibenzoyl methane derivatives include 4-tert-butyl-4'-methoxy dibenzoyl methane (e.g. "Parsol 1789"; DSM Nutrition Japan) and the like.

Examples of β,β-diphenyl acrylate derivatives include octocrylene (e.g. "Uvinul N539T"; BASF) and the like.

Examples of benzophenone derivatives include benzophenone-1 (e.g. "Uvinul 400"; BASF), benzophenone-2 (e.g. "Uvinul D50"; BASF), benzophenone-3 or oxybenzone-3 (e.g. "Uvinul M40"; BASF), benzophenone-4 (e.g. "Uvinul MS40"; BASF), benzophenone-5, benzophenone-6 (e.g. "Helisorb 11"; Norquay), benzophenone-8 (e.g. "Spectra-Sorb UV-24"; American Cyanamid), benzophenone-9 (e.g. "Uvinul DS-49"; BASF), benzophenone-12 and the like.

Examples of benzylidene camphor derivatives include 3-benzylidene camphor (e.g. "Mexoryl SD"; Chimex), 4-methylbenzylidene camphor, benzylidene camphor sulfonic acid (e.g., "Mexoryl SL"; Chimex), camphor benzalkonium methosulfate (e.g. "Mexoryl SO"; Chimex), terephthalylidene dicamphor sulfonic acid (e.g. "Mexoryl SX"; Chimex), polyacrylamide methylbenzylidene camphor (e.g. "Mexoryl SW"; Chimex) and the like.

Examples of phenylbenzimidazole derivatives include phenylbenzimidazole sulfonic acid (e.g. "Eusolex 232"; Merck), disodium phenyldibenzimidazole tetrasulfonate (e.g. "Neo Heliopan AP"; Haarmann & Reimer) and the like.

Examples of triazine derivatives include bis-ethylhexyloxyphenol methoxyphenyl triazine (e.g. "Tinosorb S"; Ciba Specialty Chemicals), ethylhexyl triazone (e.g. "Uvinul T150"; BASF), diethylhexyl butamido triazone (e.g. "Uvasorb HEB"; Sigma 3V), 2,4,6-tris(diisobutyl-4'-aminobenzalmalonate)-s-triazine, 2,4,6-tris[4-(2-ethylhexyloxycarbonyl)anilino]-1,3,5-triazine and the like.

Examples of phenylbenzotriazole derivatives include drometrizole trisiloxane (e.g. "Silatrizole"; Rhodia Chimie), methylene bis(benzotriazolyl tetramethylbutyl phenol) (e.g. "Tinosorb M" (Ciba Specialty Chemicals)) and the like.

Examples of anthranil derivatives include menthyl anthranilate (e.g. "Neo Heliopan MA"; Haarmann & Reimer) and the like.

Examples of imidazoline derivatives include ethylhexyl dimethoxybenzylidene dioxoimidazoline propionate and the like.

Examples of benzalmalonate derivatives include polyorganosiloxanes having benzalmalonate functional groups (e.g. Polysilicone-15; "Parsol SLX"; DSM Nutrition Japan) and the like.

Examples of 4,4-diarylbutadiene derivatives include 1,1-dicarboxy (2,2'-dimethylpropyl)-4,4-diphenylbutadiene and the like.

Particularly preferred examples include, but are not limited to, ultraviolet absorbing agents such as ethylhexyl methoxycinnamate, octocrylene, dimethicodiethyl benzalmalonate, polysilicone-15, 4-tert-butyl-4'-methoxy dibenzoyl methane (t-butyl methoxy dibenzoyl methane), ethylhexyl triazone, diethylamino hydroxybenzoyl hexyl benzoate, bis-ethylhexyloxyphenol methoxyphenyl triazine, oxybenzone-3, methylene bis(benzotriazolyl tetramethylbutyl phenol), phenylbenzimidazole sulfonic acid, 3-(4'-methylbenzylidene)-d,l-camphor, 3-benzylidene-d,l-camphor, homosalate and ethylhexyl salicylate. The ultraviolet absorbing agent used in the present invention may be blended in as one type or as a combination of two or more types. Of the above, good ultraviolet protection increase effects can be obtained when at least octocrylene is included as component (A).

However, when 4-tert-butyl-4'-methoxy dibenzoyl methane is blended, the blended amount thereof should preferably be 10% by mass or less relative to the total amount of component (A). This is because 4-tert-butyl-4'-methoxy dibenzoyl methane has a tendency to hinder the increase in ultraviolet protection effects due to heating when the (B) alkylene oxide derivative and the (C) ester oil are added, thus making it difficult to actually experience enhancement of the ultraviolet protection effects due to heat.

The ultraviolet scattering agent used in the present invention is not particularly limited, but specific examples include fine-particle metal oxides such as, for example, zinc oxide, titanium oxide, iron oxide, cerium oxide and tungsten oxide.

The ultraviolet scattering agent may be non-surface-treated or may be treated with various types of hydrophobic surface treatments, but those that are hydrophobically surface-treated are preferably used. As the surface treatment agent, it is possible to use a type that is commonly used in the cosmetics field including, for example, a silicone such as dimethicone and alkyl-modified silicone, an alkoxysilane such as octyltriethoxysilane, a dextrin fatty acid ester such as dextrin palmitate, or a fatty acid such as stearic acid.

The (A) ultraviolet protectant in the present invention includes embodiments consisting only of an ultraviolet absorbing agent, embodiments consisting only of an ultraviolet scattering agent, and embodiments including both an ultraviolet absorbing agent and an ultraviolet scattering agent.

Although the blended amount of the (A) ultraviolet protectant is not particularly limited, the amount should normally be at least 5% by mass, for example, 5% to 40% by mass, preferably 6% to 40% by mass, and more preferably 7% to 35% by mass relative to the total amount of the cosmetic composition. If the blended amount of the (A) ultraviolet protectant is less than 5% by mass, then sufficient ultraviolet protection effects are difficult to obtain, and even if more than 40% by mass is blended, an increase in the ultraviolet protection effects commensurate with the blended amount cannot be expected, and the stability is worsened, so it is not favorable for the blended amount to be in these ranges.

<(B) Alkylene Oxide Derivative>

The (B) alkylene oxide derivative (hereinafter sometimes referred to simply as "component (B)") that is blended in the emulsion cosmetic of the present invention is preferably a polyoxyalkylene/polyoxyethylene copolymer dialkyl ether represented by the following formula (I):

$$R_1O—[(AO)_m(EO)_n]—R_2 \qquad (I)$$

In the above formula, AO denotes an oxyalkylene group having 3 to 4 carbon atoms. Specific examples include an oxypropylene group, an oxybutylene group, an oxyisobutylene group, an oxytrimethylene group and an oxytetramethylene group, among which an oxypropylene group and an oxybutylene group are preferred. EO represents an oxyethylene group.

$R_1$ and $R_2$, each independently, represent a hydrogen atom or a hydrocarbon group having one to four carbon atoms. Examples of hydrocarbon groups include methyl groups, ethyl groups, n-propyl groups, isopropyl groups, n-butyl groups, sec-butyl groups and tert-butyl groups. Methyl groups and ethyl groups are preferred.

The $R_1$ and $R_2$ in each molecule may be the same type of hydrocarbon group, a mixture of a hydrocarbon group and a hydrogen atom, or a mixture of multiple hydrocarbon groups having different numbers of carbon atoms. However, for each of $R_1$ and $R_2$, the ratio between the numbers of hydrocarbon groups and hydrogen atoms that are present should be such that the ratio (Y/X) of the number (Y) of hydrogen atoms to the number (X) of hydrocarbon groups is preferably 0.15 or lower, and more preferably 0.06 or lower.

The symbol m represents the average number of moles of AO added, such that $1 \leq m \leq 70$, preferably $2 \leq m \leq 20$, and more preferably $2 \leq m \leq 10$. The symbol n represents the average number of moles of EO added, such that $1 \leq n \leq 70$, preferably $2 \leq n \leq 20$, and more preferably $2 \leq n \leq 10$. Additionally, m+n is 40 or less, preferably 25 or less, and more preferably 20 or less.

The order of addition of AO and EO is not particularly limited. AO and EO may be added in the form of blocks so as to form a block copolymer, or may be randomly added so as to form a random copolymer. Block copolymers include not only copolymers with two blocks, but also those with three or more blocks. Preferably, a random copolymer is used for the purpose of obtaining stable ultraviolet protection performance effects.

The molecular weight of the polyoxyalkylene/polyoxyethylene copolymer dialkyl ether represented by formula (I) should be 100 to 10000, preferably 150 to 5000, more preferably 200 to 3000, and even more preferably 300 to 2000. The ratio [EO/(AO+EO)] of the amount of EO to the total amount of AO and EO in each molecule is preferably 20% to 80% by mass.

Specific examples of polyoxyalkylene/polyoxyethylene copolymer dialkyl ethers that can be favorably used in the present invention include, but are not limited to, the following polyoxypropylene/polyoxyethylene copolymer dimethyl ethers:

PEG/PPG-9/2 dimethyl ether
PEG/PPG-17/4 dimethyl ether
PEG/PPG-14/7 dimethyl ether
PEG/PPG-11/9 dimethyl ether
PEG/PPG-55/28 dimethyl ether
PEG/PPG-36/41 dimethyl ether
PEG/PPG-6/3 dimethyl ether
PEG/PPG-8/4 dimethyl ether
PEG/PPG-6/11 dimethyl ether
PEG/PPG-14/27 dimethyl ether The polyoxyalkylene/polyoxyethylene copolymer dialkyl ethers tend to have better ultraviolet protection performance increase effects due to heat as the molecular weight becomes relatively smaller. Therefore, among the polyoxypropylene/polyoxyethylene copolymer dimethyl ethers listed above, PEG/PPG-9/2 dimethyl ether and the like exhibits the strongest effects.

The blended amount of the (B) alkylene oxide derivative should be at least 1% by mass or more, more preferably 2% by mass or more, even more preferably 3% by mass or more, and yet more preferably 5% by mass or more, and 30% by mass or less, more preferably 25% by mass or less, and more preferably 20% by mass or less relative to the total amount of the emulsion cosmetic. If the blended amount is less than 1% by mass, then there are cases in which ultraviolet protection performance increase effects due to heat cannot be sufficiently obtained. If the amount exceeds 30% by mass, then the stability and the usability may be affected.

<(C) Ester Oil>

The (C) ester oil (hereinafter sometimes referred to simply as "component (C)") blended in the emulsion cosmetic of the present invention may be an ester oil that is normally blended in cosmetics. Examples include diisopropyl sebacate, isopropyl myristate, cetyl ethylhexanoate, octyldodecyl myristate, isopropyl palmitate, butyl stearate, hexyl laurate, myristyl myristate, decyl oleate, hexyldecyl dimethyl octanoate, isononyl isononanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkylglycol monoisostearate, neopentyl glycol dicaprate, diisostearyl malate, glycerin di-2-heptyl undecanoate, trimethylolpropane tri-2-ethylhexanoate, trimethylolpropane triisostearate, pentaerythritol tetra-2-ethylhexanoate, glyceryl tri-2-ethylhexanoate (triethylhexanoin), cetyl isooctanoate, cetyl 2-ethylhexanoate, 2-ethylhexyl palmitate, (C12 to C15) alkyl benzoate, cetearyl isononanoate, glycerin tri (caprylate/caprate), butylene glycol (dicaprylate/caprate), glycerin trimyristate, glyceride tri-2-heptylundecanoate, castor oil fatty acid methyl ester, oleyl oleate, cetostearyl alcohol, acetoglyceride, 2-heptylundecyl palmitate, diisobutyl adipate, N-lauroyl-L-glutamic acid 2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, di-2-ethylheyl succinate, ethyl acetate, butyl acetate, amyl acetate, triethyl citrate, 2-ethylhexyl paramethoxycinnamate, tripropylene glycol dipivalate, 2-ethylhexyl 2-cyano-3,3-diphenyl acrylate and the like.

Among the above, for the purpose of obtaining sufficient effects of increasing the ultraviolet protection performance due to heat, the (C) ester oil used in the present invention should preferably be one having an IOB value of 0.3 or higher, such as propylene glycol dicaprylate (IOB=0.32), di-2-ethylhexyl succinate (IOB=0.32), pentaerythritol tetra-2-ethylhexanoate (IOB=0.35), glyceryl tri-2-ethylhexanoate (IOB=0.36), pentaerythritol tetra-octanoate (IOB=0.35), diisopropyl sebacate (IOB=0.40) and tripropylene glycol dineopentanoate (IOB=0.52).

In this case, IOB is an abbreviation for Inorganic/Organic Balance, which is a value representing the ratio of the inorganic value to the organic value, and which serves as an indicator of the degree of polarity of an organic compound. The IOB value is specifically represented by IOB value=inorganic value/organic value. Regarding the "inorganic value" and the "organic value" respectively, an "inorganic value" and an "organic value" are set for various types of atoms or functional groups so that, for example, the "organic value" is 20 for one carbon atom in a molecule and the "inorganic value" is 100 for one hydroxyl group. The IOB value of an organic compound can be computed by summing the "inorganic values" and the "organic values" of all of the atoms and functional groups in that organic compound (see, for example, Yoshio Koda, "*Yuki Gainenzu—Kiso to Oyo*—" [Organic Conceptual Diagram—Fundamentals and Applications], pp. 11-17, Sankyo Shuppan, 1984).

As component (C) in the present invention, one or more types selected from the above-mentioned ester oils can be favorably used.

The blended amount of the (C) ester oil should be 1.0% by mass or more, for example, 1.0% to 60% by mass, preferably 3.0% to 50% by mass relative to the total amount of the emulsion cosmetic. If the blended amount is less than 1.0% by mass, then there are cases in which ultraviolet protection performance increase effects due to heat cannot be sufficiently obtained. If the amount exceeds 60% by mass, then the stability and the usability may be affected.

<Optional Blended Components>

Aside from the above-mentioned components (A) to (C), components that are normally used in cosmetics may be blended into the emulsion cosmetic of the present invention within a range not compromising the effects of the present invention. For example, it is possible to appropriately blend polyhydric alcohols, lower alcohols, oil phase thickeners, surfactants, oils other than (C), powder components and the like.

<Polyhydric Alcohols>

Polyhydric alcohols, like the above-mentioned component (B), are often blended into normal cosmetics as humectants. In the emulsion cosmetic of the present invention, when the aforementioned component (B) and a polyhydric alcohol are combined and blended, the increase in the ultraviolet protection effects after heat has been applied becomes prominent.

The polyhydric alcohol that is blended in the present invention preferably has an ether bond. By having an ether bond, the polyhydric alcohol can be expected to more easily dissolve in water than those not having an ether bond, while also being able to dissolve in oil.

Examples of the polyhydric alcohols that can be used in the present invention include the polyalkylene glycols of formula (II) below, as well as butylene glycol, dipropylene glycol, diglycerin, propanediol, erythritol, xylitol, methylglyceth-10, sorbitol and the like.

In this case, the polyalkylene glycols are represented by the following formula (II):

$$HO(RO)_pH \tag{II}$$

In the above formula, RO denotes an oxyalkylene group having two to four carbon atoms, and p is 3 to 500.

Specifically, it is selected from among those that are used in cosmetics, and includes polyethylene glycol (also represented by "PEG"), polypropylene glycol (also represented by "PPG") and polybutylene glycol (also represented by "PBG") and the like.

Among the above, polyethylene glycols in which, in formula (I) above, RO is an oxyethylene group, and p is in the range 3 to 500, more preferably 3 to 60, are preferred. The preferred average molecular weight of the polyethylene glycol is within the range 150 to 23000, more preferably 150 to 3000. Specific examples include polyethylene glycol 300, polyethylene glycol 400, polyethylene glycol 1500, polyethylene glycol 20000 and the like.

The polyalkylene glycol tends to have better ultraviolet protection performance increase effects due to heat as the molecular weight becomes relatively smaller. Therefore, among the polyethylene glycols listed above, particularly strong effects are obtained when polyethylene glycol 300 or polyethylene glycol 400 is used.

In the present invention, the increase in the ultraviolet protection effects due to heat becomes prominent when containing a combination of, for example, a low-molecular-weight polyoxypropylene/polyoxyethylene copolymer dimethyl ether having an average molecular weight of 150 to 3000 with, for example, a low-molecular-weight polyhydric alcohol derivative having an average molecular weight of 150 to 3000. Specific examples of such combinations include, in particular, a combination of PEG/PPG-9/2 dimethyl ether and polyethylene glycol 300, and a combination of PEG/PPG-9/2 dimethyl ether and polyethylene glycol 400.

The blended amount of the polyhydric alcohol should be at least 1% by mass or more, more preferably 2% by mass or more, even more preferably 3% by mass or more, and yet more preferably 5% by mass or more, and 30% by mass or less, more preferably 25% by mass or less, and even more preferably 20% by mass or less relative to the total amount of the emulsion cosmetic. If the blended amount is less than 1% by mass, then there are cases in which ultraviolet protection performance increase effects due to heat cannot be sufficiently obtained. If the amount exceeds 30% by mass, then the stability and the usability may be affected.

<Lower Alcohols>

Examples of lower alcohols include alcohols having one to five carbon atoms, such as ethanol and isopropanol. By blending a lower alcohol, the spreadability when applying the emulsion cosmetic can be improved. When a lower alcohol is blended, the blended amount may, for example, be 5% to 30% by mass relative to the total amount of the emulsion cosmetic.

<Oil Phase Thickeners>

As oil phase thickeners, substances that are used, in emulsion cosmetics and the like, as components for obtaining effects of thickening the oil phase by dissolving into oils or being swollen by oils are preferable. For example, they include dextrin fatty acid esters such as dextrin palmitate and dextrin myristate, sucrose fatty acid esters such as sucrose caprylic acid ester, solid or semi-solid hydrocarbon oils such as vaseline, hydrogenated palm oil and hydrogenated castor oil, organically modified clay minerals such as disteardimonium hectorite and benzyl dimethyl stearyl ammonium hectorite, or C8 to C22 higher fatty acids that are solid at ambient temperature, such as lauric acid, myristic acid, palmitic acid and stearic acid or salts thereof, and the like.

<Surfactants>

As a surfactant, in the case of a water-in-oil emulsion cosmetic, a surfactant having a silicone backbone (polysiloxane structure) and having an HLB lower than 8 is preferred. For example, it is preferable to use a polyether-modified silicone, a polyether/alkyl co-modified silicone, a polyglycerin-modified silicone and/or a polyglycerin/alkyl co-modified silicone, among which a polyether-modified silicone or a polyether/alkyl co-modified silicone is more preferred.

Meanwhile, in the case of an oil-in-water emulsion cosmetic, the surfactant may be of one or more types selected from among non-ionic surfactants that are conventionally used in oil-in-water emulsion cosmetics, among which those having an HLB of 6 or higher are preferably used. In particular, one containing polyoxyethylene hardened castor oil is particularly preferred for the purposes of stability of the preparation and absorbance increase effects due to contact with moisture. Specific examples of polyoxyethylene hardened castor oils include PEG-10 hydrogenated castor oil, PEG-20 hydrogenated castor oil, PEG-25 hydrogenated castor oil, PEG-30 hydrogenated castor oil, PEG-40 hydrogenated castor oil, PEG-50 hydrogenated castor oil, PEG-60 hydrogenated castor oil, PEG-80 hydrogenated castor oil, PEG-100 hydrogenated castor oil and the like. If a polyoxyethylene hardened castor oil is not to be included, then a non-ionic surfactant having an HLB of 8 or higher, preferably 10 or higher, and more preferably 12 or higher is preferably used.

<Oils Other than Aforementioned Ester Oils>

Additionally, the emulsion cosmetic of the present invention may further include, aside from the aforementioned (C) ester oil, volatile oils or non-volatile oils that are normally used in cosmetics.

Volatile oils include volatile hydrocarbon oils and volatile silicone oils.

The volatile hydrocarbon oils are not particularly limited as long as they are hydrocarbon oils that are volatile at ambient temperature (25° C.) and that are conventionally used in cosmetics and the like. Specific examples include isododecane, isohexadecane, hydrogenated polyisobutene and the like.

The volatile silicone oils are silicone oils that are volatile at ambient temperature (25° C.) and that are conventionally used in cosmetics and the like, including cyclic dimethylpolysiloxanes having four to six silicon atoms and chain dimethylpolysiloxanes having two to five silicon atoms. Specific examples include cyclic silicone oils such as hexamethylcyclotrisiloxane (D3), octamethyltetracyclosiloxane (D4), decamethylcyclopentasiloxane (D5) and dodecamethylcyclohexasiloxane (D6), diphenylsiloxyphenyl trimethicone, volatile dimethicone (as commercially available products, KF-96L-1.5cs and KF-96L-2cs; manufactured by Shin-Etsu Chemical) and the like.

Non-volatile oils include, for example, hydrocarbon oils, vegetable oils, high-molecular-weight polyoxyalkylene glycols and silicone oils.

Specific examples include liquid oils and fats such as palm oil, linseed oil, camellia oil, macadamia nut oil, corn oil, olive oil, avocado oil, sasanqua oil, castor oil, safflower oil, apricot kernel oil, cinnamon oil, jojoba oil, grape oil, almond oil, rapeseed oil, sesame oil, sunflower oil, wheat germ oil, rice germ oil, rice bran oil, cottonseed oil, soybean oil, peanut oil, tea seed oil, evening primrose oil, egg yolk oil, liver oil, triglycerin, glyceryl trioctanoate, glyceryl tri-isopalmitate, isostearic acid and the like; hydrocarbon oils such as hydrogenated polyisobutene, liquid paraffin, squalane and hydrogenated polydecene; and silicone oils such as polyoxybutylene polyoxypropylene glycol and non-volatile dimethicone (as a commercially available product, KF-96A-6cs; manufactured by Shin-Etsu Chemical) and the like.

<Spherical Powder>

Additionally, a spherical powder is preferably further contained. By blending a spherical powder, stickiness is suppressed, the texture is improved, and a good, silky touch can be obtained. The spherical powder may be arbitrarily used without any particular restrictions, as long as it is of a type that is blended into cosmetic products or the like in general. Examples include (meth)acrylic acid ester resin powders, polyamide resin powders (nylon powders), polyethylene powders, polystyrene powders, copolymer resin powders of styrene and (meth)acrylic acid, benzoguanamine resin powders, polytetrafluoroethylene powders, cellulose powders, trimethyl silsesquioxane powders and the like, as well as organopolysiloxane elastomer spherical powders or composite spherical powders having the above as base powders. The average particle size of the spherical powder is preferably 3 to 20 μm. If the size is smaller than 3 μm, then an effect of suppressing stickiness cannot be observed, and if the size is larger than 20 μm, then graininess conversely occurs. The blended amount of the spherical powder is not particularly limited, but is preferably 3% to 30% by mass, more preferably 7% to 20% by mass.

An example of a commercially available spherical organic resin powder is Ganzpearl (AICA Kogyo), and examples of commercially available spherical silicone resin powders include Trefil E-505C, Trefil E-506C, Trefil E-506S, Trefil HP40T (all Toray Dow Corning Silicone), Tospearl 2000B (Momentive Performance Materials), silicone powders KSP-100 and KSP-300 (Shin-Etsu Chemical), and the like.

Additionally, aside from the above, components that are normally used in cosmetics may be blended into the emulsion cosmetic of the present invention within a range not compromising the effects of the present invention, in accordance with the format being prepared. For example, it is possible to appropriately blend, as needed, humectants (including polyhydric alcohols other than those mentioned above, e.g., glycerin), oil gelling agents (for example, hydroxystearic acid, dibutyllauroyl glutamide and polyamide-8), polysaccharides, emulsifiers, thickeners, pH adjusters, chelating agents, preservatives, antioxidants, oil-based active agents, alcohols, colorants, pigments, medicinal agents and the like. Examples of medicinal agents include ascorbic acid (vitamin C), tranexamic acid, kojic acid, ellagic acid, albutin, alkoxysalicylic acid, nicotinic acid amide, glycyrrhizinic acid, tocopherol, retinol, and salts or derivatives of the above (e.g., sodium L-ascorbate, L-ascorbic acid ester magnesium salts, L-ascorbic acid glucoside, 2-O-ethyl-L-ascorbic acid, 3-O-ethyl-L-ascorbic acid, 4-methoxysalicylic acid sodium salts, 4-methoxysalicylic acid potassium salts, dipotassium glycyrrhizinate, stearyl glycyrrhizinate, tocopherol acetate, retinol acetate, retinol palmitate, etc.).

The emulsion cosmetic of the present invention may be provided in the form of an oil-in-water emulsion cosmetic or a water-in-oil emulsion cosmetic. Specific formats include milky lotions, creams and sprays, which may be produced by using conventional methods appropriate for the respective formats.

The cosmetic of the present invention may be applied not only to sunscreen cosmetics, but also to a makeup base or a makeup cosmetic such as a foundation provided with sunscreen effects, a hair cosmetic (including various types of hair-care products such as hairsprays and hair treatments for protecting the hair or scalp from ultraviolet rays), a spray-type cosmetic or the like.

The emulsion cosmetic of the present invention has the novel property in which the ultraviolet protection effects of a coating film are increased by heat. In this case, "the ultraviolet protection effects are increased by heat" refers to the case in which the thermal reaction rate, as determined by the following expression, from an absorbance integral value of a pre-heat treatment coating film (unheated sample) from 280 to 400 nm measured with a spectrophotometer or the like and an absorbance integral value of a post-heat treatment coating film (heated sample) that has been similarly measured, exceeds 100%.

$$\text{Thermal reaction rate (\%)}=\text{(post-heat treatment absorbance integral value)/(pre-heat treatment absorbance integral value)} \times 100$$

In the emulsion cosmetic of the present invention, the thermal reaction rate exceeds at least 100%, preferably at least 103%, more preferably at least 105%, even more preferably at least 110%, and particularly preferably at least 115%.

When investigating the increase in the ultraviolet protection effects due to heat, the heating temperature should preferably be within the range from 30° C. to 70° C. For example, the temperature may be 32° C. or higher, 35° C. or higher, 37° C. or higher, or 40° C. or higher, and 65° C. or lower, 60° C. or lower, 55° C. or lower, or 50° C. or lower. If the heating temperature exceeds 70° C., then there may be problems such as a resin-composed measurement plate melting or the like.

In order to accurately evaluate the impact of heat, the heating time should preferably be 1 minute or longer, more preferably 10 minutes or longer. The upper limit of the heating time is not particularly limited, but should normally be 60 minutes or shorter, preferably 30 minutes or shorter.

EXAMPLES

Hereinafter, the present invention will be explained in further detail by providing specific examples. However, the present invention is not limited to the examples below. Additionally, the blended amounts in the following examples and the like are indicated in percentage by mass where not particularly indicated otherwise. Before specifically explaining each example, the evaluation method that was used will be explained. Post-thermal irradiation absorbance integral value change (thermal reaction rate)

Prepared emulsion cosmetics were dripped, in the amount of 2 mg/cm², onto skin-simulating PMMA plates (SPFMASTER-PA01), applied with a finger for 60 seconds, and dried for 15 minutes to form coating films. Using an uncoated plate as a control, the absorbances (280 to 400 nm) of the coating films were measured with a Hitachi U-3500 self-recording spectrophotometer, and the obtained measurement data was used to determine pre-heat treatment absorbance integral values.

Next, the plates having the coating films were placed in isothermic tanks for 30 minutes at 37° C., and the absorbance integral values were determined in a manner similar to the above.

The changes (thermal reaction rate) in the absorbance integral values from before to after thermal irradiation were computed from the following equation.

$$\text{Thermal reaction rate (\%)}=\text{(post-heat treatment absorbance integral value)/(pre-heat treatment absorbance integral value)} \times 100$$

The values of the thermal reaction rates (%) of the respective samples are also indicated in the tables below.

(1) Water-In-Oil Emulsion Cosmetic

The water-in-oil emulsion cosmetic compositions indicated in Table 1 below were prepared. Specifically, the oil-based components were mixed by using a homomixer, the powders were dispersed therein, and the well-mixed water-based components were thereafter added to obtain the compositions.

TABLE 1

| | Test Ex. 1 | Test Ex. 2 | Test Ex. 3 | Test Ex. 4 | Test Ex. 5 | Test Ex. 6 |
|---|---|---|---|---|---|---|
| Ion-exchanged water | bal | bal | bal | bal | bal | bal |
| Ethanol | 5 | 5 | 5 | 5 | 5 | 5 |
| Glycerin | 1 | 1 | 1 | 1 | 1 | 1 |
| PEG/PPG-9/2 dimethyl ether | 0.2 | 0.5 | 1 | 3 | 5 | 10 |
| Disteardimonium hectorite | 0.3 | 0.3 | 0.3 | 0.3 | 0.3 | 0.3 |
| PEG-9 polydimethyl siloxy-ethyl dimethicone | 2 | 2 | 2 | 2 | 2 | 2 |
| Isostearic acid | 0.5 | 0.5 | 0.5 | 0.5 | 0.5 | 0.5 |
| Diisopropyl sebacate | 10 | 10 | 10 | 10 | 10 | 10 |
| Volatile dimethicone | 20 | 20 | 20 | 20 | 20 | 20 |
| Ethylhexyl methoxycinnamate | 10 | 10 | 10 | 10 | 10 | 10 |
| Hydrophobically treated fine-particle titanium oxide | 2 | 2 | 2 | 2 | 2 | 2 |
| Hydrophobically treated fine-particle zinc oxide | 10 | 10 | 10 | 10 | 10 | 10 |
| Spherical silicone resin powder | 7 | 7 | 7 | 7 | 7 | 7 |
| Chelating agent | s.a. | s.a. | s.a. | s.a. | s.a. | s.a. |
| Total | 100 | 100 | 100 | 100 | 100 | 100 |
| Thermal reaction rate (%) | 100% | 102% | 110% | 115% | 121% | 127% |

As shown in Table 1, it was confirmed that, by blending in an alkylene oxide derivative, the ultraviolet protection effects due to heat were at least the pre-heat treatment values. Additionally, a sufficient increase in the ultraviolet protection effects was obtained by blending in at least 1% by mass. Furthermore, as the blended amount of the alkylene oxide derivative was increased, the rate of increase in the effects thereof became higher.

The water-in-oil emulsion cosmetic compositions indicated in Table 2 below were prepared in the same manner as in Table 1.

TABLE 2

| | Test Ex. 7 | Test Ex. 8 | Test Ex. 9 |
|---|---|---|---|
| Ion-exchanged water | bal | bal | bal |
| Ethanol | 10 | 10 | 10 |
| PEG/PPG-9/2 dimethyl ether | 5 | — | — |
| PEG/PPG-14/7 dimethyl ether | — | 5 | — |
| PEG/PPG-17/4 dimethyl ether | — | — | 5 |
| Disteardimonium hectorite | 0.5 | 0.5 | 0.5 |
| PEG-9 polydimethyl siloxy-ethyl dimethicone | 2 | 2 | 2 |

TABLE 2-continued

| | Test Ex. 7 | Test Ex. 8 | Test Ex. 9 |
|---|---|---|---|
| Isostearic acid | 1 | 1 | 1 |
| Diisopropyl sebacate | 5 | 5 | 5 |
| Volatile dimethicone | 20 | 20 | 20 |
| Octocrylene | 5 | 5 | 5 |
| bis-Ethylheyloxyphenol methoxyphenyl triazine | 1 | 1 | 1 |
| Diethylamino hydroxybenzoyl hexyl benzoate | 1 | 1 | 1 |
| Ethylhexyl triazone | 1 | 1 | 1 |
| Ethylhexyl methoxycinnamate | 5 | 5 | 5 |
| Hydrophobically treated fine-particle titanium oxide | 2 | 2 | 2 |
| Hydrophobically treated fine-particle zinc oxide | 10 | 10 | 10 |
| Spherical silicone resin powder | 7 | 7 | 7 |
| Chelating agent | s.a. | s.a. | s.a. |
| Total | 100 | 100 | 100 |
| Thermal reaction rate (%) | 117% | 108% | 104% |

As shown in Table 2, it was confirmed that, by blending in an alkylene oxide derivative, the ultraviolet protection effects were increased by heat. In particular, a tendency for the ultraviolet protection effects due to heat to largely increase when the molecular weight (m+n) of the alkylene oxide derivative was smaller was observed.

The water-in-oil emulsion cosmetic compositions indicated in Table 3 below were prepared in the same manner as in Table 1.

As shown in Table 3, it was confirmed that, by blending in an alkylene oxide derivative, the ultraviolet protection effects were increased by heat. Furthermore, the increase in the ultraviolet protection effects due to heat was prominent when a polyhydric alcohol derivative was combined with an alkylene oxide derivative. In particular, extremely strong effects were obtained by a combination of PEG/PPG-9/2 dimethyl ether and polyethylene glycol 300 (Test example 12) and a combination of PEG/PPG-9/2 dimethyl ether and polyethylene glycol 400 (Test example 13).

The water-in-oil emulsion cosmetic compositions indicated in Table 4 below were prepared in the same manner as in Table 1.

TABLE 4

| | Test Ex. 16 | Test Ex. 17 | Test Ex. 18 | Test Ex. 19 |
|---|---|---|---|---|
| Ion-exchanged water | bal | bal | bal | bal |
| Ethanol | 10 | 10 | 10 | 10 |
| Glycerin | 1 | 1 | 1 | 1 |
| Polyethylene glycol 300 | 0.5 | 0.5 | 0.5 | 0.5 |
| PEG/PPG-9/2 dimethyl ether | 10 | 10 | 10 | 10 |
| Disteardimonium hectorite | 0.3 | 0.3 | 0.3 | 0.3 |
| PEG-9 polydimethyl siloxy-ethyl dimethicone | 3 | 3 | 3 | 3 |
| Isostearic acid | 1 | 1 | 1 | 1 |
| Diisopropyl sebacate | 10 | 10 | 10 | 10 |
| Volatile dimethicone | 20 | 20 | 20 | 20 |
| Ethylhexyl methoxycinnmate | 10 | 10 | 10 | 10 |
| t-Butyl methoxy dibenzoyl methane | — | 0.5 | 1 | 2 |

TABLE 3

| | Test Ex. 10 | Test Ex. 11 | Test Ex. 12 | Test Ex. 13 | Test Ex. 14 | Test Ex. 15 |
|---|---|---|---|---|---|---|
| Water | bal | bal | bal | bal | bal | bal |
| Ethanol | 10 | 10 | 10 | 10 | 10 | 10 |
| Glycerin | 1 | 1 | 1 | 1 | 1 | 1 |
| PEG/PPG-9/2 dimethyl ether | — | 5 | 5 | 5 | 5 | 5 |
| Polyethylene glycol 300 | — | — | 5 | — | — | — |
| Polyethylene glycol 400 | — | — | — | 5 | — | — |
| Polyethylene glycol 1500 | — | — | — | — | 5 | — |
| Polyethylene glycol 20000 | — | — | — | — | — | 5 |
| Disteardimonium hectorite | 0.5 | 0.5 | 0.5 | 0.5 | 0.5 | 0.5 |
| Dextrin palmitate | 1 | 1 | 1 | 1 | 1 | 1 |
| PEG-9 polydimethyl siloxyethyl dimethicone | 2 | 2 | 2 | 2 | 2 | 2 |
| Isostearic acid | 1 | 1 | 1 | 1 | 1 | 1 |
| Diisopropyl sebacate | 5 | 5 | 5 | 5 | 5 | 5 |
| Cyclomethicone | 5 | 5 | 5 | 5 | 5 | 5 |
| Volatile dimethicone | 15 | 10 | 5 | 5 | 5 | 5 |
| Non-volatile dimethicone | 3 | 3 | 3 | 3 | 3 | 3 |
| Isododecane | 5 | 5 | 5 | 5 | 5 | 5 |
| Octocrylene | 4 | 4 | 4 | 4 | 4 | 4 |
| bis-Ethylheyloxyphenol methoxyphenyl triazine | 1 | 1 | 1 | 1 | 1 | 1 |
| Diethylamino hydroxybenzoyl hexyl benzoate | 1 | 1 | 1 | 1 | 1 | 1 |
| Ethylhexyl triazone | 6 | 6 | 6 | 6 | 6 | 6 |
| Hydrophobically treated fine-particle titanium oxide | 4 | 4 | 4 | 4 | 4 | 4 |
| Hydrophobically treated fine-particle zinc oxide | 10 | 10 | 10 | 10 | 10 | 10 |
| Spherical silicone rubber powder | 3 | 3 | 3 | 3 | 3 | 3 |
| Hydrophobically treated talc | 3 | 3 | 3 | 3 | 3 | 3 |
| Spherical crosslinked PMMA powder | 3 | 3 | 3 | 3 | 3 | 3 |
| Spherical silica | 3 | 3 | 3 | 3 | 3 | 3 |
| Chelating agent | s.a. | s.a. | s.a. | s.a. | s.a. | s.a. |
| Total | 100 | 100 | 100 | 100 | 100 | 100 |
| Thermal reaction rate (%) | 98% | 129% | 140% | 135% | 131% | 124% |

TABLE 4-continued

| | Test Ex. 16 | Test Ex. 17 | Test Ex. 18 | Test Ex. 19 |
|---|---|---|---|---|
| Hydrophobically treated fine-particle titanium oxide | 2 | 2 | 2 | 2 |
| Hydrophobically treated fine-particle zinc oxide | 10 | 10 | 10 | 10 |
| Spherical silicone resin powder | 7 | 7 | 7 | 7 |
| Chelating agent | s.a. | s.a. | s.a. | s.a. |
| Total | 100 | 100 | 100 | 100 |
| Thermal reaction rate (%) | 127% | 123% | 118% | 113% |

As shown in Table 4, a high thermal reaction rate was obtained when t-butyl methoxy dibenzoyl methane was not blended as the (A) ultraviolet protectant, and in the cases in which it was blended, when the blended amount thereof was 10% by mass or less relative to the total amount of the (A) ultraviolet protectants.

The water-in-oil emulsion cosmetic compositions indicated in Table 5 below were prepared in the same manner as in Table 1.

TABLE 5

| | Test Ex. 20 | Test Ex. 21 | Test Ex. 22 |
|---|---|---|---|
| Ion-exchanged water | 22.1 | 22.1 | 22.1 |
| Ethanol | 5 | 5 | 5 |
| Glycerin | 1 | 1 | 1 |
| PEG/PPG-9/2 dimethyl ether | 10 | 10 | 10 |
| Disteardimonium hectorite | 0.3 | 0.3 | 0.3 |
| PEG-9 poly dimethyl siloxy-ethyl dimethicone | 2 | 2 | 2 |
| Isostearic acid | 0.5 | 0.5 | 0.5 |
| Diisopropyl sebacate | 10 | 10 | 10 |
| Cetyl 2-ethylhexanoate | 7 | 5 | — |
| Volatile dimethicone | 20 | 20 | 20 |
| Octocrylene | 3 | 5 | 10 |
| Hydrophobically treated fine-particle titanium oxide | 2 | 2 | 2 |
| Hydrophobically treated fine-particle zinc oxide | 10 | 10 | 10 |
| Spherical silicone resin powder | 7 | 7 | 7 |
| Chelating agent | 0.1 | 0.1 | 0.1 |
| Total | 100 | 100 | 100 |
| Thermal reaction rate (%) | 102% | 103% | 106% |

As shown in Table 5, in the cases in which octocrylene was blended as the (A) ultraviolet protectant, higher thermal reaction rates were obtained when the blended amount of the octocrylene was greater.

(2) Oil-In-Water Emulsion Cosmetic

The oil-in-water emulsion cosmetic composition indicated in Table 6 below was prepared. Specifically, the oil-based components were mixed by using a homomixer, the powders were dispersed therein, and the well-mixed water-based components were thereafter added to obtain the composition.

TABLE 6

| | Test Ex. 23 |
|---|---|
| Water | bal |
| Glycerin | 4 |
| 1,3-Butylene glycol | 7 |
| PEG/PPG-9/2 dimethyl ether | 5 |

TABLE 6-continued

| | Test Ex. 23 |
|---|---|
| Polyethylene glycol 300 | 1 |
| Succinoglycan | 0.3 |
| (Dimethyl acrylamide/sodium acryloyl dimethyl taurate) cross-polymer | 0.3 |
| Sucrose fatty acid ester | 3 |
| PEG-60 hydrogenated castor oil | 2 |
| Diisopropyl sebacate | 2 |
| Non-volatile dimethicone | 2 |
| Cyclomethicone | 12 |
| Triethylhexanoin | 5 |
| Isostearic acid | 1 |
| Sorbitan sesquiisostearate | 0.5 |
| Hydrophobically treated fine-particle zinc oxide | 10 |
| Ethylhexyl methoxycinnamate | 10 |
| Diethylamino hydroxybenzoyl hexyl benzoate | 1 |
| bis-Ethylheyloxyphenol methoxyphenyl triazine | 1 |
| Spherical urethane resin powder | 3 |
| pH adjuster | s.a. |
| Chelating agent | s.a. |
| Preservative | s.a. |
| Total | 100 |
| Thermal reaction rate (%) | 106% |

As shown in Table 6, the ultraviolet protection effects were observed to be increased by heat even in a cosmetic in an oil-in-water emulsion format.

The oil-in-water emulsion cosmetic compositions indicated in Table 7 below were prepared in the same manner as in Table 6.

TABLE 7

| | Test Ex. 24 | Test Ex. 25 | Test Ex. 26 | Test Ex. 27 |
|---|---|---|---|---|
| Water | bal | bal | bal | bal |
| Glycerin | 4 | 4 | 4 | 4 |
| 1,3-Butylene glycol | 7 | 7 | 7 | 7 |
| PEG/PPG-9/2 dimethyl ether | 6 | 6 | 6 | 6 |
| Succinoglycan | 0.3 | 0.3 | 0.3 | 0.3 |
| (Dimethyl acrylamide/sodium acryloyl dimethyl taurate) cross-polymer | 0.3 | 0.3 | 0.3 | 0.3 |
| Sucrose fatty acid ester | 3 | 3 | 3 | 3 |
| PEG-60 hydrogenated castor oil | 2 | 2 | 2 | 2 |
| Diisopropyl sebacate | 2 | 2 | 2 | 2 |
| Non-volatile dimethicone | 2 | 2 | 2 | 2 |
| Cyclomethicone | 12 | 12 | 12 | 12 |
| Triethylhexanoin | 5 | 5 | 5 | 5 |
| Isostearic acid | 1 | 1 | 1 | 1 |
| Sorbitan sesquiisostearate | 0.5 | 0.5 | 0.5 | 0.5 |
| Hydrophobically treated fine-particle zinc oxide | 10 | 10 | 10 | 10 |
| Ethylhexyl methoxycinnamate | 10 | 10 | 10 | 10 |
| Diethylamino hydroxybenzoyl hexyl benzoate | 1 | 1 | 1 | 1 |
| bis-Ethylheyloxyphenol methoxyphenyl triazine | 1 | 1 | 1 | 1 |
| 4-tert-Butyl-4'-methoxy dibenzoyl methane | 0.5 | 1 | 2 | 3 |
| Spherical urethane resin powder | 3 | 3 | 3 | 3 |
| pH adjuster | s.a. | s.a. | s.a. | s.a. |
| Chelating agent | s.a. | s.a. | s.a. | s.a. |
| Preservative | s.a. | s.a. | s.a. | s.a. |
| Total | 100 | 100 | 100 | 100 |
| Thermal reaction rate (%) | 112% | 110% | 107% | 103% |

As shown in Table 7, even in cosmetics in an oil-in-water emulsion format, high thermal reaction rates were obtained in the cases in which t-butyl methoxy dibenzoyl methane was blended as the (A) ultraviolet protectant, when the blended amount thereof was 10% by mass or less relative to the total amount of the (A) ultraviolet protectants.

Hereinafter, examples of formulations of the cosmetic of the present invention will be indicated. Needless to say, the present invention is not limited in any way by these formulation examples, and is as defined by the claims. The blended amounts are all indicated in percentage by mass relative to the total amount of the cosmetic.

Formulation Example 1: Two-layer makeup base

| (Component name) | Blended amount (% by mass) |
|---|---|
| Purified water | balance |
| Ethanol | 5 |
| PEG/PPG-9/2 dimethyl ether | 5 |
| Glycerin | 1 |
| Xylitol | 1 |
| *Potentilla erecta* extract | 0.3 |
| Sodium hyaluronate | 0.1 |
| 2-O-ethyl-L-ascorbic acid | 0.1 |
| Dipotassium glycyrrhizinate | 0.05 |
| Isododecane | 3 |
| Diisopropyl sebacate | 10 |
| PBG/PPG-9/1 copolymer | 1 |
| Dimethicone | 13 |
| Caprylyl methicone | 3 |
| Highly polymerized aminopropyl dimethicone 20% dimethicone solution | 1 |
| Trifluoroalkyl dimethyl trimethyl siloxysilicic acid 50% dimethicone solution | 3 |
| Dextrin palmitate | 0.5 |
| Ethylhexyl methoxycinnamate | 7 |
| Octocrylene | 5 |
| Diethylamino hydroxybenzoyl hexyl benzoate | 1 |
| bis-Ethylhexyloxyphenol methoxyphenyl triazine | 0.5 |
| Hydrophobically treated fine-particle titanium oxide | 2 |
| Hydrophobically treated fine-particle zinc oxide | 5 |
| Hydrophobically treated pigment-grade titanium oxide | 1 |
| Hydrophobically treated iron oxide | 0.07 |
| Methyl methacrylate cross-polymer | 2 |
| (Vinyl dimethicone/methicone silsesquioxane) cross-polymer | 2 |
| Hydrophobically treated talc | 2 |
| PEG-9 polydimethyl polysiloxyethyl dimethicone | 1.5 |
| PEG/PPG-19/19 dimethicone | 0.3 |
| Dimethyl distearyl ammonium hectorite | 0.4 |
| Isostearic acid | 0.3 |
| EDTA•3Na | s.a. |
| Table salt | s.a. |
| Sodium pyrosulfite | s.a. |
| Tocopherol | s.a. |
| Fragrance | s.a. |

Formulation example 2: Cream-type foundation

| (Component name) | Blended amount (% by mass) |
|---|---|
| Purified water | balance |
| Ethanol | 5 |
| Phenoxyethanol | 1 |
| PEG/PPG-9/2 dimethyl ether | 5 |
| Glycerin | 3 |
| Erythritol | 1 |
| Xylitol | 1 |
| *Potentilla erecta* extract | 1 |
| Glycylglycine | 0.1 |
| Tranexamic acid | 1 |
| Dipotassium glycyrrhizinate | 0.05 |
| Tripropylene glycol pivalate | 2 |
| Diisopropyl sebacate | 5 |
| Dimethicone | 10 |
| Cyclomethicone | 5 |

18

-continued

Formulation example 2: Cream-type foundation

| (Component name) | Blended amount (% by mass) |
|---|---|
| Trisiloxysilicic acid 50% cyclopentasiloxane solution | 2 |
| Dextrin palmitate | 1 |
| Ethylhexyl methoxycinnamate | 7 |
| Hydrophobically treated fine-particle titanium oxide | 3 |
| Hydrophobically treated fine-particle zinc oxide | 3 |
| Hydrophobically treated pigment-grade titanium oxide | 6 |
| Hydrophobically treated iron oxide | 3.2 |
| Hydrophobically treated barium sulfate-coated titanated mica | 0.01 |
| Hydrophobically treated titanated mica | 0.01 |
| Dimethicone cross-polymer 13% cyclopentasiloxane mixture | 2 |
| Polymethyl silsesquioxane | 2 |
| Methyl methacrylate cross-polymer | 2 |
| Hydrophobically treated fine-particle silica | 0.5 |
| Lauryl PEG-9 polydimethyl polysiloxyethyl dimethicone | 2 |
| (Dimethicone/(PEG-10/15)) cross-polymer | 1 |
| Dimethyl distearyl ammonium hectorite | 1 |
| Isostearic acid | 0.2 |
| Tocopherol | s.a. |
| EDTA•3Na | s.a. |
| Table salt | s.a. |
| Sodium pyrosulfite | s.a. |
| Fragrance | s.a. |

Formulation example 3: Aerosol spray-type sunscreen

| (Component name) | Blended amount (% by mass) |
|---|---|
| Purified water | balance |
| Ethanol | 5 |
| Polyethylene glycol 300 | 2 |
| Silica | 0.5 |
| Glycerin | 1 |
| PEG/PPG-14/7 dimethyl ether | 6 |
| DL-α-tocopherol acetate | 0.5 |
| D-glutamic acid | 0.1 |
| Stearyl glycyrrhizinate | 0.1 |
| Isododecane | 10 |
| Glyceryl tri-2-ethylhexanoate | 5 |
| Isopropyl myristate | 3 |
| Diisopropyl sebacate | 5 |
| PBG/PPG-9/1 copolymer | 1 |
| Dimethicone | 13 |
| Trisiloxysilicic acid 50% cyclopentasiloxane solution | 0.5 |
| Sucrose tetrastearate triacetate | 0.5 |
| Dextrin palmitate | 1 |
| Ethylhexyl methoxycinnamate | 5 |
| Diethylamino hydroxybenzoyl hexyl benzoate | 2 |
| bis-Ethylhexyloxyphenol methoxyphenyl triazine | 1 |
| Polysilicone-15 | 2 |
| Octocrylene | 5 |
| Methyl methacrylate cross-polymer | 5 |
| (Vinyl dimethicone/methicone silsesquioxane) cross-polymer | 3 |
| Hydrophobically treated talc | 1 |
| Cetyl PEG/PPG-10/1 dimethicone | 1 |
| Lauryl PEG-9 polydimethyl polysiloxyethyl dimethicone | 1 |
| Dimethyl distearyl ammonium hectorite | 0.5 |
| Isostearic acid | 0.3 |
| Sorbitan sesquiisostearate | 0.3 |
| EDTA•3Na | s.a. |

-continued

| Formulation example 3: Aerosol spray-type sunscreen | |
|---|---|
| (Component name) | Blended amount (% by mass) |
| Tocopherol | s.a. |
| Fragrance | s.a. |

The above-mentioned components were mixed to form a stock solution, and a spray can was filled with the stock solution and LPG at a ratio of 50:50 to obtain an aerosol spray-type sunscreen.

| Formulation example 4: Gel-type BB cream | |
|---|---|
| (Component name) | Blended amount (% by mass) |
| Purified water | balance |
| Ethanol | 8 |
| PEG/PPG-9/2 dimethyl ether | 5 |
| Rosa roxburghii extract | 0.1 |
| Stearoxyhydroxypropylmethylcellulose | 0.2 |
| (Dimethylacrylamide/sodium acryloyldimethyl taurate) copolymer | 0.2 |
| Succinoglucan | 0.1 |
| Glycerin | 3 |
| Polyethylene glycol 300 | 1 |
| bis-PEG-18 methyl ether dimethyl silane | 3 |
| PEG/PPG-14/7 dimethyl ether | 1 |
| Ethylhexyl methoxycinnamate | 10 |
| Diisopropyl sebacate | 5 |
| Diethylamino hydroxybenzoyl hexyl benzoate | 1 |
| bis-Ethylhexyloxyphenol methoxyphenyl triazine | 3 |
| Hydrophobically treated fine-particle titanium oxide | 3 |
| Hydrophobically treated fine-particle zinc oxide | 5 |
| Hydrophobically treated pigment-grade titanium | 4 |
| Hydrophobically treated iron oxide | 0.4 |
| Isopropyl myristate | 2 |
| Polypropylene glycol (17) | 2 |
| Di(cholesteryl/phytosteryl) N-lauroyl-L-glutamate | 0.5 |
| Dextrin (palmitate/ethylhexanoate) | 0.5 |
| Fragrance | s.a. |
| Silica | 1 |

| Formulation example 5: Milky lotion - cream type BB cream | |
|---|---|
| (Component name) | Blended amount (% by mass) |
| Purified water | balance |
| Ethanol | 6 |
| Magnesium L-ascorbyl phosphate | 0.5 |
| Acetylated sodium hyaluronate | 0.1 |
| Water-soluble collagen | 0.1 |
| Rosa roxburghii extract | 0.1 |
| (Dimethylacrylamide/sodium acryloyldimethyl taurate) copolymer | 0.3 |
| Succinoglucan | 0.2 |
| Cellulose gum | 0.2 |
| Glycerin | 2 |
| Butylene glycol | 4 |
| PEG/PPG-14/7 dimethyl ether | 3 |
| PEG/PPG-9/2 dimethyl ether | 2 |
| Polyethylene glycol 300 | 1 |
| Polyoxyethylene hardened castor oil (100 mole) | 1 |
| Polyoxyethylene (8 mole) behenyl ether | 1 |
| Sodium stearoyl methyltaurate | 0.1 |
| Stearyl alcohol | 0.5 |
| Behenyl alcohol | 0.5 |
| Ethylhexyl methoxycinnamate | 8 |
| Octocrylene | 2 |
| Ethylhexyl triazine | 1 |

-continued

| Formulation example 5: Milky lotion - cream type BB cream | |
|---|---|
| (Component name) | Blended amount (% by mass) |
| Diethylamino hydroxybenzoyl hexyl benzoate | 1 |
| bis-Ethylhexyloxyphenol methoxyphenyl triazine | 1 |
| Isododecane | 10 |
| Diisopropyl sebacate | 5 |
| Dimethicone | 2 |
| Phytosteryl macadamiate | 1 |
| Di(phytosteryl/octyldodecyl) N-lauroyl-L-glutamate | 0.5 |
| Dextrin (palmitate/ethylhexanoate) | 0.5 |
| Hydrophobically treated fine-particle zinc oxide | 8 |
| Pigment-grade hydrophobically treated titanium oxide | 4 |
| Hydrophobically treated iron oxide | 0.2 |
| Isostearic acid | 0.5 |
| Sorbitan sesquiisostearate | 0.5 |
| EDTA-2Na•H2O | s.a. |
| Sodium hexametaphosphate | s.a. |
| Citric acid | s.a. |
| Sodium citrate | s.a. |
| Fragrance | s.a. |
| Talc | 3 |
| Silica | 3 |

The invention claimed is:

1. An emulsion cosmetic comprising (A) 7 to 35% by mass of an ultraviolet protectant;

(B) 5 to 20 mass % of polyethylene glycol (PEG)/polypropylene glycol (PPG)-9/2 dimethyl ether;

(C) 3.0 to 50% by mass of an ester oil having an IOB value of 0.3 or higher, and (D) water;

wherein the (A) ultraviolet protectant comprises an ultraviolet absorbing agent and an ultraviolet scattering agent; the ultraviolet absorbing agent comprises at least one of octocrylene, bis-ethylheyloxyphenol methoxyphenyl triazine, diethylamino hydroxybenzoyl hexyl benzoate, ethylhexyl triazone and 4-tert-butyl-4'-methoxy dibenzoyl methane, the ultraviolet scattering agent comprises at least one of hydrophobically treated titanium oxide and hydrophobically treated zinc oxide, and wherein when the (A) ultraviolet protectant comprises 4-tert-butyl-4'-methoxy dibenzoyl methane, a blended amount of 4-tert-butyl-4'-methoxy dibenzoyl methane in the (A) ultraviolet protectant is 10% by mass or less relative to a total amount of the (A) ultraviolet protectant, wherein the cosmetic is a water-in-oil emulsion cosmetic;

wherein the cosmetic does not comprise ethylhexyl methoxycinnamate, and wherein the cosmetic does not comprise phenylbenzimidazole sulfonic acid.

2. The emulsion cosmetic as in claim 1, wherein the component (B) is a random copolymer.

3. The emulsion cosmetic as in claim 1, wherein the (A) ultraviolet protectant comprises at least octocrylene.

4. The emulsion cosmetic as in claim 1, further comprising (E) a polyethylene glycol having an average molecular weight of 150 to 3000.

5. The emulsion cosmetic as in claim 1, wherein the ester oil is selected from the group consisting of propylene glycol dicaprylate, di-2-ethylhexyl succinate, pentaerythritol tetra-2-ethylhexanoate, glyceryl tri-2-ethylhexanoate, pentaerythritol tetra-octanoate, diisopropyl sebacate and tripropylene glycol dineopentanoate.

6. The emulsion cosmetic as in claim 1, wherein a thermal reaction rate of the cosmetic is at least 110%.

7. The emulsion cosmetic as in claim 5, wherein a thermal reaction rate of the cosmetic is at least 110%.

8. The emulsion cosmetic as in claim 1, further comprising 5 to 30 mass % of an alcohol having one to five carbon atoms; and 7 to 20 mass % of a spherical organic resin powder.

9. The emulsion cosmetic as in claim 8, wherein a thermal reaction rate of the cosmetic is at least 110%.

* * * * *